United States Patent [19]

Cuppoletti et al.

[11] Patent Number: 5,208,649
[45] Date of Patent: May 4, 1993

[54] ASSEMBLY FOR FRONT FACE TESTING

[75] Inventors: John Cuppoletti; Nick H. Langdon, both of Cincinnati, Ohio

[73] Assignee: University of Cincinnati, Cincinnati, Ohio

[21] Appl. No.: 839,469

[22] Filed: Feb. 20, 1992

[51] Int. Cl.⁵ .................. G01N 21/01; G01N 21/64
[52] U.S. Cl. .................. 356/244; 250/461.2; 356/318
[58] Field of Search .................. 356/244, 317, 318; 250/458.1, 461.1, 461.2

[56] References Cited

U.S. PATENT DOCUMENTS

| | | | |
|---|---|---|---|
| 4,008,397 | 2/1977 | Zdrodowski | 250/373 |
| 4,279,509 | 7/1981 | Daffern | 356/246 |
| 4,531,834 | 7/1985 | Nogami | 356/73 |
| 4,989,974 | 2/1991 | Anton et al. | 356/246 |
| 5,074,662 | 12/1991 | Sullivan | 356/244 |

OTHER PUBLICATIONS

Biomedical Article from Jan. 10, 1989, entitled "Measurement of Calcium in a Cultured Monolayer of Heart-cells".

Article entitled "Fluorescence probe measurement of the intralysosomal pH in living cells and the perturbation of pH by various agents" Proc. Natl. Acad. Sci. USA, vol. 75 #7 pp. 3327–3331, Jul. 1978, Cell Biology.

Primary Examiner—Vincent P. McGraw
Attorney, Agent, or Firm—Frost & Jacobs

[57] ABSTRACT

A coverslip holder assembly for a front face fluorimetry flow cell has a holder body and a hingedly attached clamp for releasably maintaining a coverslip adjacent the front face of the holder body and flow cell. The assembly is preferably a unitary arrangement wherein the clamp is hingedly mounted adjacent the bottom end of the front face of the holder body, and has a convenient snap lock release mechanism at its top end to selectively lock the coverslip in flush arrangement with the front face. The holder assembly can provide a biased snug fit with a variety of cuvettes or similar sample vessels, and enables the use of highly colored or fluorescent compounds for perfusion in front face fluorimetry operations.

20 Claims, 5 Drawing Sheets

ASSEMBLY FOR FRONT FACE TESTING

TECHNICAL FIELD

This invention relates to flow cells for fluorimetry and similar procedures for measuring various characteristics of cultured monolayers of cells, and, more particularly, to an assembly for mounting a coverslip upon which cells have been cultured for undertaking fluorimetry or the like, wherein the assembly includes a holder body and a hingedly attached coverslip clamp which conveniently and releasably locks the coverslip adjacent an optical pathway closely adjacent the front of a flow cell and normal to the incident light directed onto the cells.

BACKGROUND ART

Devices for measuring the light absorbing, reflecting, fluorescing, and other optical characteristics of substances such as tissue cells in suspension or cultured on a coverslip, are often used to measure the presence and concentration of particular substances, which can be helpful such as in various biomedical and physiological contexts. For example, a cuvette-based fluorometer system has been used to measure the presence and concentration of substances (e.g., $Ca^{2+}$) in biological cells such as cardiac cells, wherein the cells are cultured on a coverslip fixed into a predetermined position within the cuvette.

In the past, however, such coverslips have been mounted at an angle to incoming excitation light, and fluorescence or other optical characteristics induced by the excitation light is received by a monitor device (such as an emission monochromator) situated at an angle of approximately 90 degrees to the incoming excitation light path. Generally this angled orientation between the incident excitation light and the emitted fluorescence or other optical phenomenon was utilized to minimize contamination of monitored emissions by the incoming excitation light. Once the coverslip is fixed in a diagonal manner, the volume of solution in the cuvette is often perfused, such as through inlet and outlet tubes and a peristaltic pump.

An example of the predetermined angular arrangement of excitation light relative to the monitored emissions is shown in U.S. Pat. No. 4,008,397, which issued to J. Zdrodowski. In this patent, a fluorimeter flow cell is described as being constructed entirely of clear plastic tubing, as opposed to utilizing the more traditional quartz flow cells. The plastic tubing is essentially transparent to ultra-violet light at a predetermined wavelength which is passed through an inlet aperture to impinge upon the material in the tube. If fluorescent material is present in the tube, the fluorescent radiation will be emitted from the tubing through an outlet aperture oriented at 90 degrees to the entry aperture.

Another fluorimeter utilizing a flow cell is shown in U.S. Pat. No. 4,531,834 which issued to T. Nogami. Again in the Nogami flow cell, fluorescent light is emitted at a 90 degree angle to the incident light for reception by a photocell. A processor compares and utilizes the detected transmission light and the intensity of the fluorescent light to automatically compensate for variation of intensity of the light source.

U.S. Pat. No. 4,989,974 which issued to K. Anton et al., describes the diverse use of flow cells for liquid chromatography (LC), supercritical fluid chromatography (SFC), gas chromatography (GC) and capillary zone electrophoresis (CZE) in order to provide measurements and analysis of predefined volumes of sample solutions in a known environment. Anton et al. describe the fact that gaps between the flow cell and the detector can often lead to increased background noise and drift phenomenon during measurement procedures. The micro-flow cell described by Anton et al. provides two diametrically opposite light permeable passages on a holding device comprising two substantially identical shell halves. Incident light is permitted to pass through one of the light permeable passages, while a photoconductor is attached to an adjacent passage. The adjacent passages are located at 90 degree angles to one another, whereby measured luminescence or the like is again received at a 90 degree angle to the incident light.

Consequently, while the use of flow cell devices is widespread and well known in the industry for use in conjunction with a sample vessel such as a cuvette and devices for measuring light absorbing, fluorescence, and reflecting characteristics of cell material; heretofore, there has not been provided a coverslide device satisfactory for front face testing procedures. Moreover, prior art arrangements tended to allow for inexact gaps between the coverslips or other sample cell arrangements and the emission detector devices utilized to monitor optical phenomenon. As the prior art specifically suggests, such variations often allow for unacceptable levels of interference and imprecision, and reduce the sensitivity and adaptability of the testing setup.

DISCLOSURE OF THE INVENTION

It is an object of this invention to obviate the above-described problems and shortcomings of the flow cells and coverslip holder devices heretofore available in the industry.

It is another object of the present invention to provide a flow cell for front-face fluorimetry which insures simple and reliable mounting and location of coverslips for front-face fluorimetry and other optical testing.

It is yet another object of the present invention to provide a holder assembly for a coverslip which is adapted for use in conjunction with a cuvette for front-face fluorimetry, wherein a releasable clamp is assembled with a holder body to maintain a coverslip closely adjacent to the front-face of the cuvette and substantially normal to the path of incident light.

It is also an object of the present invention to provide an assembly for holding a coverslip within a cuvette or other sample vessel in conjunction with a device for measuring the light absorbing, fluorescence, and reflecting characteristics of the cells, wherein the assembly includes a clamp hingedly attached to a holder body for conveniently supporting a coverslip in substantially flush position relative to the front face of the cuvette.

It is yet another object of the present invention to provide a holder assembly of relatively simple construction which provides convenient and reliable mounting of a coverslip adjacent the front face of a cuvette in relatively normal relationship with incident light thereon, wherein the assembly comprises a clamp and holder body which are hingedly attached and which include a locking device to selectively snap the clamp in attached position relative to the holder body.

In accordance with one aspect of the present invention there is provided a holder assembly for a coverslip upon which cells may be cultured for study, wherein the holder is adapted for use in conjunction with a sample vessel and a device for measuring the light absorbing, fluorescence, and/or reflecting characteristics of the cells. The holder includes a holder body having spaced front and rear faces, top and bottom ends, and a light permeable path extending through the holder between the front and rear surfaces. The front face has a substantially planar portion, and, in a preferred embodiment, includes a ledge located adjacent the bottom end for supporting a coverslip substantially flush with the planar portion. A clamp is releasably attachable to the holder body and maintains the coverslip in its substantially flush supported position when in attached position. The clamp includes a light permeable portion aligned with the path of the holder body when in attached position to obviate interference with incident light on these monolayer cells of the coverslip in use.

In a preferred embodiment, the holder assembly further includes a hinged connection between the clamp and the holder body so that the clamp may be alternately articulated between open position and attached position. The hinged connection of the clamp is preferably located adjacent the bottom end of the holder body, and a snap-fit locking arrangement is provided adjacent the top end to selectively lock the clamp in attached position relative to the holder body.

The holder assembly may further be provided as a unitary structure which is effectively outwardly biased to allow the assembly to snugly conform to the inner shape of a cuvette or other sample vessel. The holder assembly further enables profusion of cells of the coverslip, such as by an arrangement of inlet and outlet tubes.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE DRAWINGS

Figure 1:
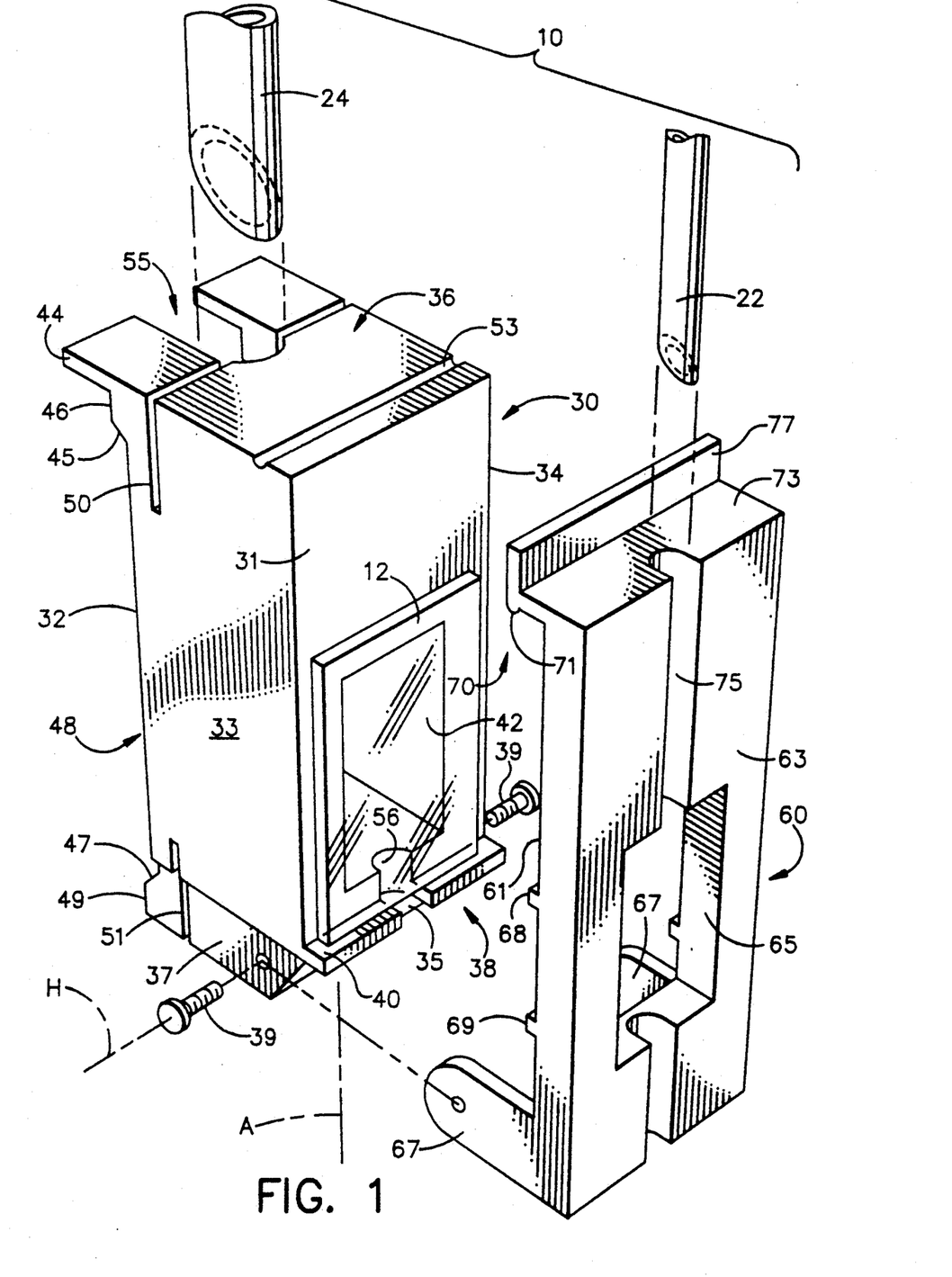
FIG. 1 is a perspective, exploded view of a coverslip holder assembly made in accordance with the present invention.

Referring now to the drawings in detail, wherein like numerals indicate the same elements throughout the views, FIG. 1 shows an exploded perspective view of an assembly 10 for holding a coverslip 12 adjacent the front-face of a sample vessel for use in front face optical analysis procedures. Particularly, assembly 10 is shown as comprising a holder body 30 and a clamp 60 which can be releasably attached or locked in attached position to support a coverslip 12 in a substantially planar position, as will be explained.

Holder body 30 is further illustrated as comprising a front face 31, rear face 32, and oppositely disposed side faces 33 and 34, respectively. At least a portion of front face 31 will preferably be provided in a substantially planar conformation for receiving a coverslip (e.g., 12) adjacent the non-reflecting light sink 42, which is preferably provided in the form of a light permeable sight path extending through holder 30 between front and rear surfaces 31 and 32. It is contemplated, however, that other non-reflecting or light permeable structures could also be successfully utilized to insure that incident light passing through a supported coverslip will not be reflected by holder 30. Obviously, light reflected by holder 30 could interfere with the sensitivity and reliability of optical analysis.

Holder body 30 is further illustrated as including a top end 36 and bottom end 38. Top end 36 also preferably includes an outwardly extending mounting lip 44, which can be conveniently designed to facilitate alignment and seating procedures of assembly 10 in a sample vessel or cuvette (e.g., 15). Adjacent bottom end 38 of front face 31, there is provided a beveled lower portion 35 to facilitate placement of holder 30 into a sample vessel and to facilitate medium circulation therearound, such as for perfusion (as will be discussed). Also adjacent bottom end 38 on front face 31, there is provided means for maintaining a coverslip in substantially flush, supported position relative to front face 31. Such support means is illustrated in FIG. 1 as including a coverslip ledge 40 extending outwardly from front face 31 to receive and support the lower edge of coverslip 12.

Figure 5:
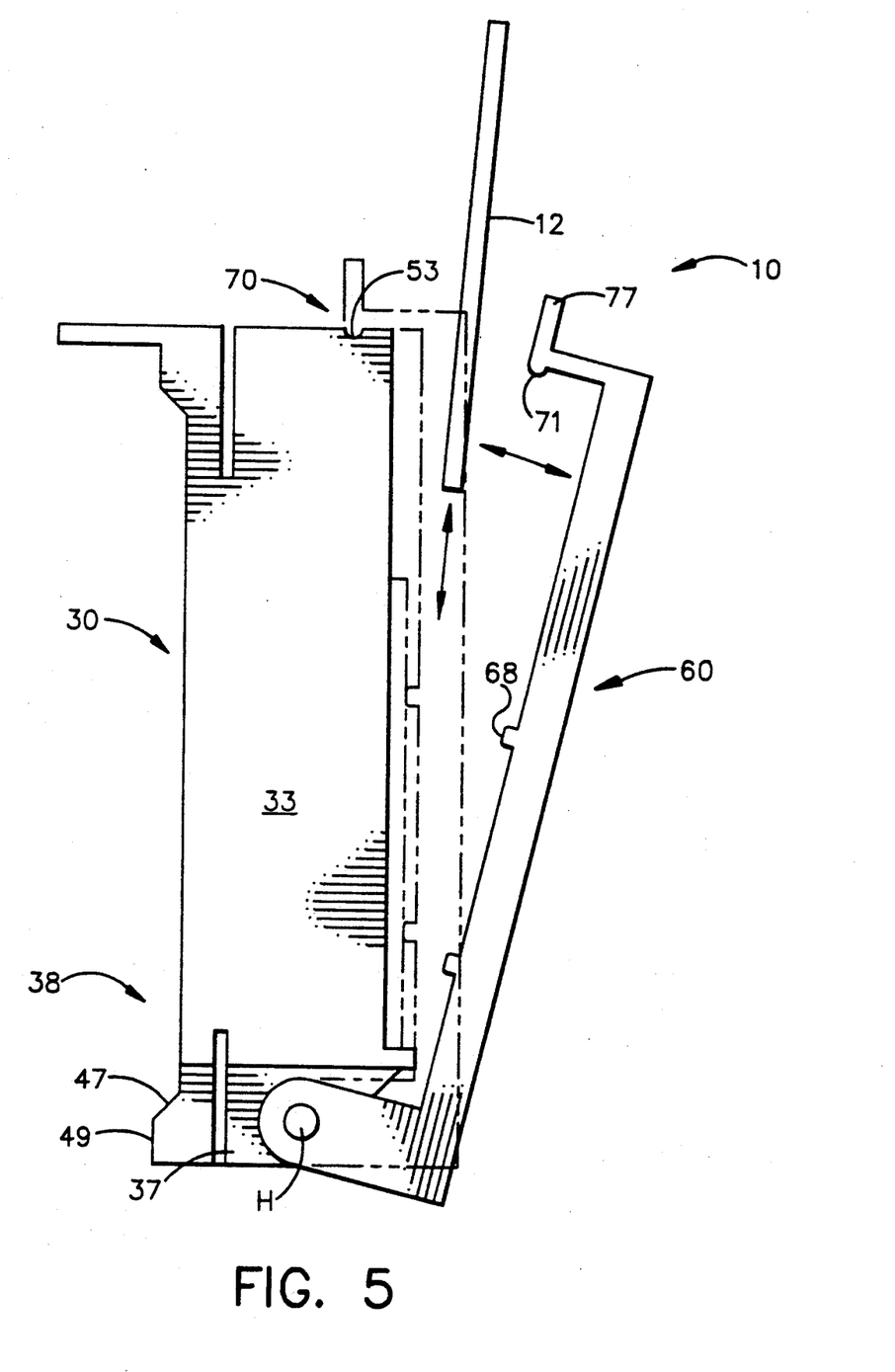
FIG. 5 is a side elevational view of a coverslip holder assembly of the present invention, illustrating coverslip insertion and removal.

As best illustrated in FIGS. 1 and 5, adjacent bottom end 38 on side faces 33 and 34, there is an oppositely disposed pair of hinge recesses 37 for enabling a preferred recessed hinged attachment of clamp 60 to holder body 30. As can be appreciated, a pair of outwardly extending hinge arms 67 are provided on clamp 60 for hinged attachment within recesses 37, such as by hinge pins 39.

Rear face 32 of holder body 30 is provided with a recessed portion 48 formed by a pair of oppositely disposed beveled surfaces 45 and 47, adjacent top and bottom ends 36 and 38, respectively. As can be appreciated from FIG. 4, when assembly 10 is inserted into a sample vessel or cuvette (e.g., 15), recessed portion 48 enables holder body 30 to be easily inserted while allowing some tolerance for variations in vessel width. This tolerance not only facilitates the insertion process, but also helps to insure that assembly 10 is adaptable to a relatively wide range of sample vessels without unnecessary binding effects on a coverslip 12 supported therewithin.

Upper sealing face 46 and lower sealing face 49 are designed to provide a relatively snug fit adjacent upper end 36 and lower end 38, respectively. It is also preferred to provide holder body 30 with one or more biasing means (e.g., 50 and 51) to augment the adaptability to a variety of standard sample vessels or cuvettes while insuring a relatively snug fit with all. As seen best in FIGS. 1, 3 and 4, upper and lower spring slots 50 and 51, respectively, are preferably incorporated to provide a predetermined limited amount of spring force or compressibility adjacent upper and lower ends 36 and 38. As will be understood, biasing means 50 and 51 thereby enable holder body 3 to be easily inserted into and removed from a variety of sample vessels having varying dimensions, while insuring the relatively snug fit with each.

Figure 3:
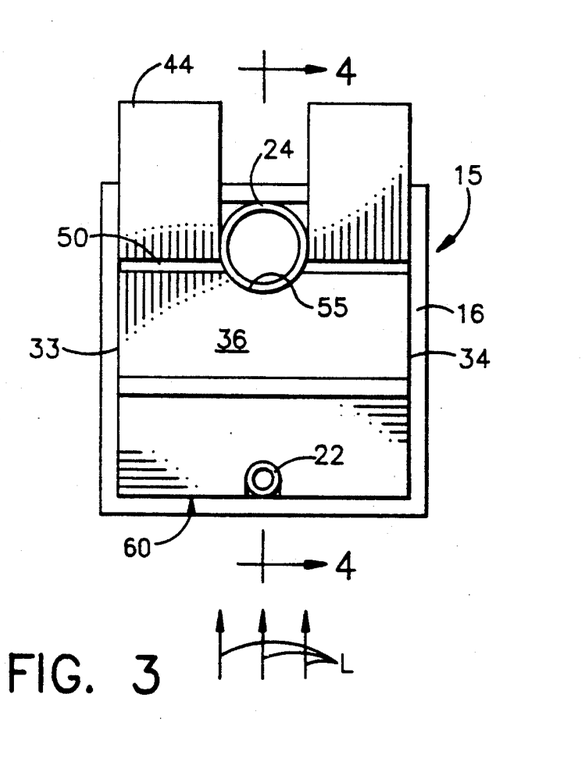
FIG. 3 is a top plan view of the coverslip holder assembly shown in FIG. 1, illustrated as mounted within a sample vessel or cuvette.
Figure 4:
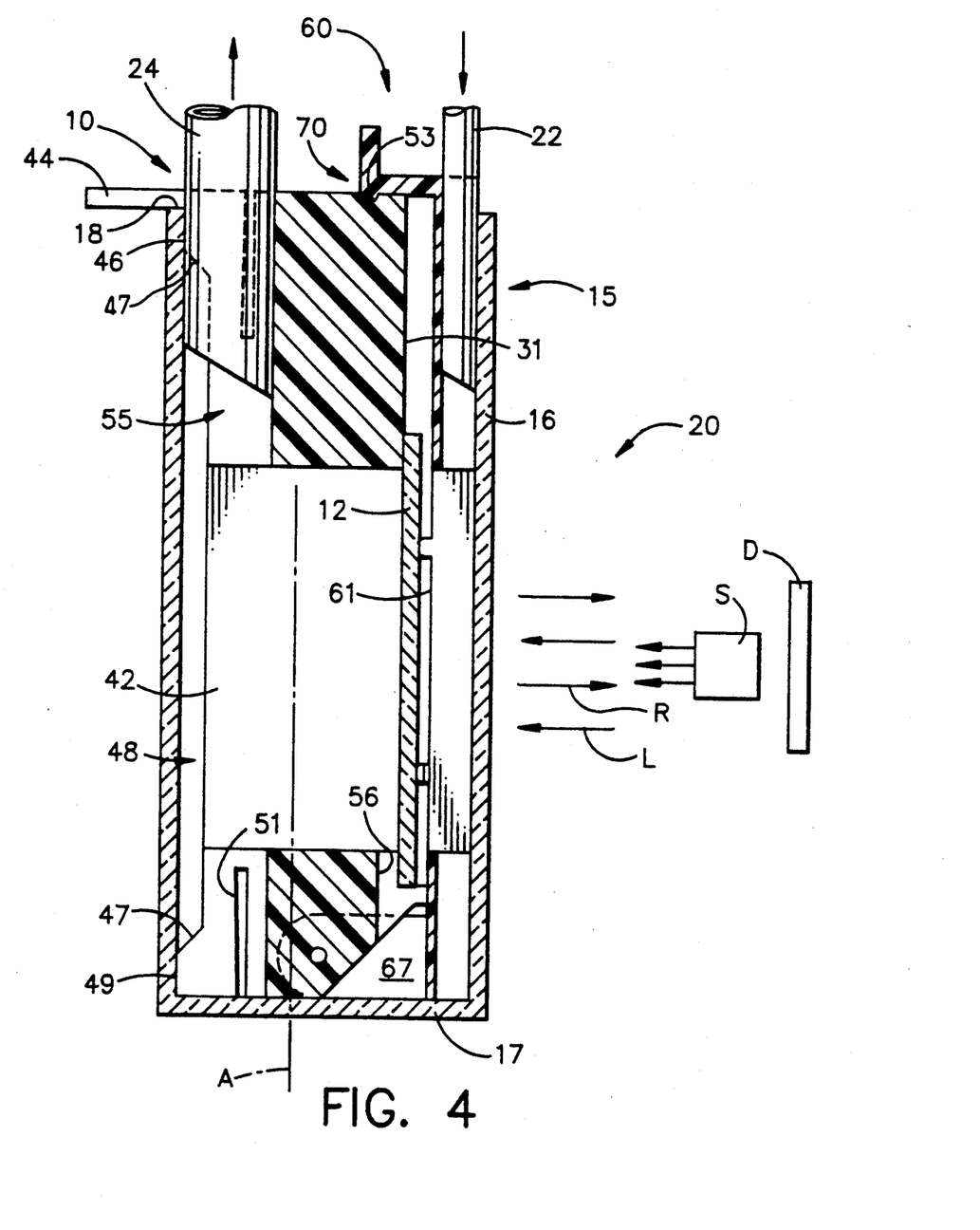
FIG. 4 is a vertical cross-sectional view of the coverslip holder assembly of FIG. 3, taken along line 4—4 thereof, and showing schematicaly an excitation light source and detector device of a front-face fluorimeter setup.

Adjacent upper end 36, there is also preferably provided a snap lock groove 53 or similar device for interacting with clamp 60 to selectively lock the clamp in attached position for supporting a coverslip 12. As illustrated in FIGS. 1, 3 and 4, a longitudinal groove or channel 55 is also preferably provided in a direction substantially parallel with longitudinal axis A to facilitate circulation of various solutions and media which may be desired or required from time to time through a sample vessel. Circulation channel 55 is shown as including a cylindrical portion for conveniently receiving a circulation tube (e.g., outlet tube 24), which may be attached in conjunction with a peristaltic pumping device or the like (not shown). A further circulation channel 56 is illustrated adjacent the lower part of front face 31 for insuring the relatively unimpeded circulation of solution within a sample vessel and around coverslip holding assembly 10.

Figure 2:
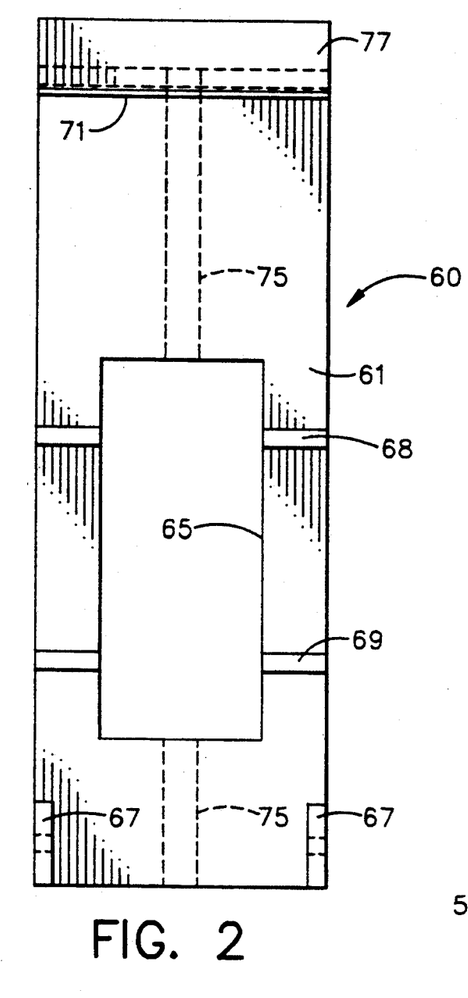
FIG. 2 is a left side elevational view of the coverslip clamp shown in FIG. 1.

As best seen in FIGS. 1, 2 and 4, clamp 60 is provided with an inner surface 61, and outer surface 63, and a light permeable, non-reflecting passage 65 which may preferably comprise an opening extending between inner and outer surfaces 61 and 63. As mentioned earlier, a pair of oppositely disposed inwardly extending hinge arms 67 are preferably provided for hingedly attaching clamp 60 adjacent the bottom end 38 of holder 30 to enable articulation of clamp 60 between attached position (FIG. 4) and open position (FIG. 5). Snap lock means 70 is preferably provided to facilitate the reliable and positive maintenance of a coverslip (e.g., 12) in substantially flush supported position relative to the front face 31 of holder body 30.

While it is contemplated that clamp 60 ca be designed to be held in attached position simply by insertion of assembly 10 into a sample vessel or cuvette (e.g., 15), it is preferred that clamp 60 have some means of being positively locked in attached position to enhance the security and reliability of a coverslip holding assembly made in accordance herewith.

As illustrated in FIGS. 1, 2 and 4, a preferred clamp snap lock arrangement 70 comprises a downwardly disposed locking ledge 71 cantilevered from the upper portions of clamp 60 via resilient arm 73, and including a manipulation tab 77 to facilitate manual unlocking procedures. As best seen in FIG. 4, once a coverslip has been placed on ledge 40 of holder body 30, clamp 60 is simply rotated inwardly into attached position, wherein locking ledge 71 is snapped into locking engagement with transverse groove 53 of body 30. Inner surface 61 preferably comprises one or more relatively flexible means for holding coverslip 12 firmly against front face 31, such as the pair of spaced laterally and inwardly extending support protuberances 68 and 69, respectively.

It is contemplated that both holder body 30 and clamp 60 will be produced of somewhat resilient material (e.g., plastic, polymer, resin or the like) to provide inherent resilience to portions of the coverslip holding assembly 10. In this regard, by hingedly mounting clamp 60 adjacent its lower edges, and providing locking means adjacent its upper edges, the mid-section and particularly the inwardly extending support protuberances (e.g., 68 and 69) will have some limited resilience in the inward/outward directions. As a result, a coverslip 12 can be effectively wedged between clamp 60 and front face 31 of holder 30 in relatively firm manner without risking damage to the coverslip or holder assembly 10.

Longitudinal circulation groove 75 is also preferably provided along outer surface 63. Groove 75 may be preferably formed in a substantially cylindrical conformation to receive a circulation supply tube (e.g., inlet tube 22), such as for a perfusion circulation system or the like.

In use, holding assembly 10 receives a coverslip 12, such as illustrated in FIG. 5, and clamp 60 is thereafter moved into attached position (see FIG. 4). Assembly 10 with its supported coverslip is then inserted into a sample vessel, such as a cuvette 15. As will be appreciated, the external shape of holder assembly 10 is preferably designed to correspond with the inner periphery of the sidewalls (e.g., 16) of a sample vessel 15. Light permeable passage 65 of clamp 60 correspondingly aligns with anti-reflecting portion 42 of holder body 30 when in attached position, whereby excitation radiation L provided from the front face of sample vessel 15 (e.g., from radiation source S) will pass through the front face (e.g., wall 16) of sample vessel 15, through passage 65, and impinge upon the cells on coverslip 12.

Incident light which passes through the cells and coverslip 12 continues through path 42 so as not to be reflected outwardly from assembly 10. Light which is reflected by the cells, or outwardly directed fluorescence or other optical phenomenon (R), proceeds outwardly of assembly 10 toward detector device D where it is monitored and/or recorded by a device 20 for assaying optical characteristics of cells (e.g., a spectrofluorimeter or the like). FIG. 4 illustrates a device 20 for measuring optical characteristics of cells in a schematic manner, as details of such devices is commonly available in the industry and not repeated here.

The present holder assembly 10 has the advantages of providing an extremely short path length between the sample coverslip and the front face of a cuvette (e.g., 15), which facilitates the use of highly colored or fluorescent compounds for perfusion. Perfusion media may variously contain drugs, hormones, fluorescent antibodies, and/or inhibitors.

Figure 6:
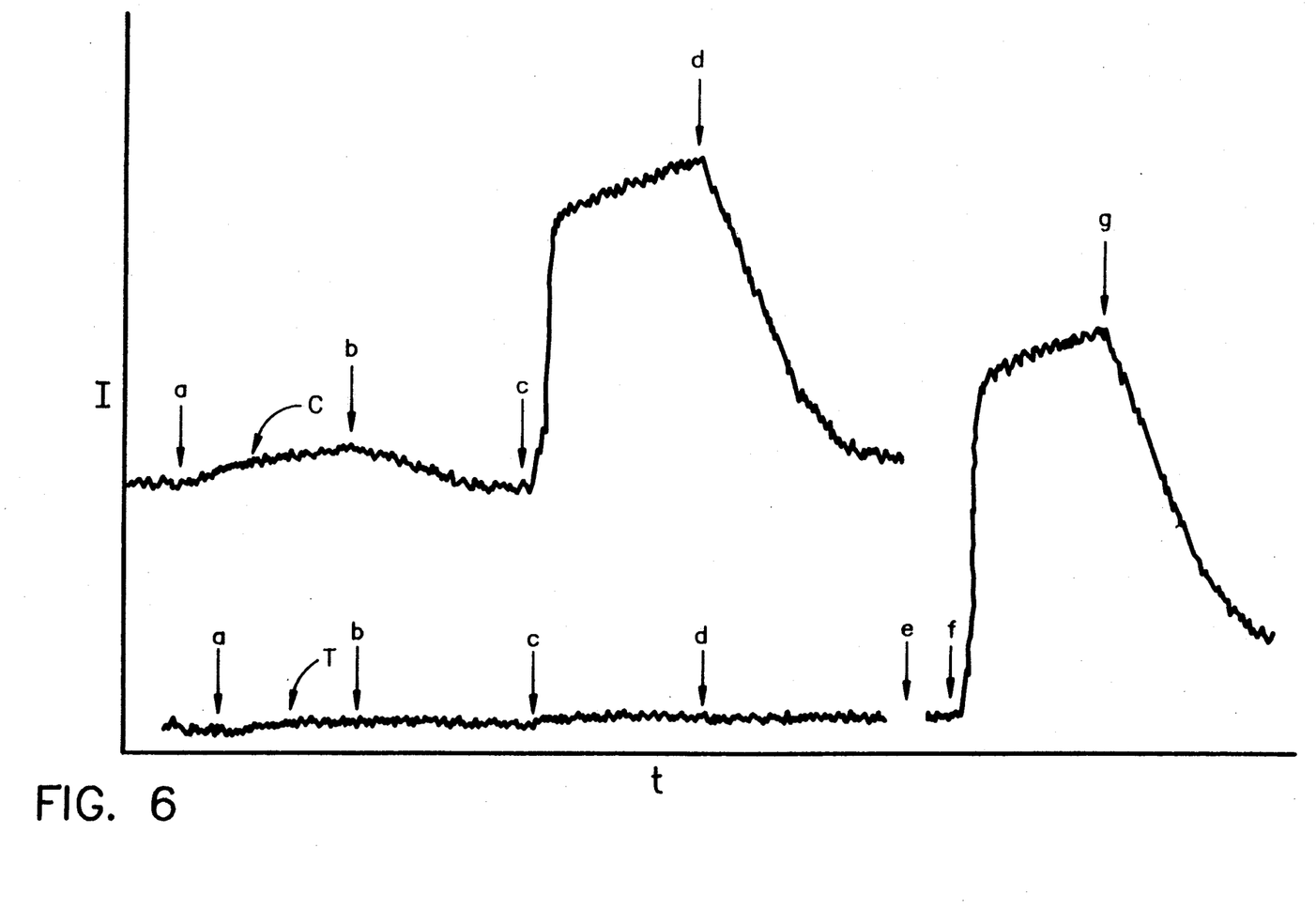
FIG. 6 is a graphical illustration of an example of front face fluorimetry results undertaken on bovine tracheal cells loaded with a 5 mM solution of SPQ fluorescent dye, wherein the vertical axis is intensity (I) of fluorescence (in cps), and the horizontal axis is time (t) (in secs).

FIG. 6 graphically illustrates results of an example wherein bovine tracheal cells were loaded with a 5mM solution of fluorescent dye [e.g., 6-mythoxy-M-(3-sulfopropyl) quinolinium, known as SPQ]. The SPQ dye is not fluorescent if chlorine is present, and the graphical illustration of the control test results (line C) shows that where perfusion procedures remove chlorine (such as at a), fluorescence activity increases even without stimulation, and when chlorine is added (such as at b) fluorescence subsides. In this control test, chlorine is removed and a stimulant of cellular functions (e.g., Isoproterenol[1] or "Iso" as available from Sigma Chemical Company, or an epinephrine isopropyl homolog) is added (at c), and upon stimulation the intensity of fluorescent activities dramatically increases until chloride is again added and the Iso stimulant is removed (at d).

[1] 4-[1-Hydroxy-2-[(1-methylethyl)-amino] ethyl]-1,2-benzenediol

The lower portion of the graph of FIG. 6 illustrates the cell test results (line T), wherein the bovine tracheal cells were loaded with the 5mM solution of SPQ as well as an inhibitor diphenylame-2-carboxylate (DPC) to inhibit the chloride channels of the cells. As can be seen, no change in intensity of fluorescence was seen despite chloride being taken away (at a), chloride being added back (at b), chloride being taken away and Iso stimulant being added (at c), and chloride being added and the Iso stimulant being taken away (at d), by perfusion procedures. After the DPC inhibitor is washed away (at e), and chloride is taken away and the Iso stimulant added (at f), a massive spike in intensity of fluorescence is seen until chloride is again added and the Iso stimulant removed (at g).

These results graphically, illustrate how the front face coverslide holder assembly facilitates vastly improved reliability and test procedure control for measuring fluorescence and other characteristics of cells in this manner. A plurality of monochrometers can be utilized as the detector device D to provide an ideal front face set up for measuring fluorescence of cells on the coverslip. As can be appreciated from the test results set forth in FIG. 6, the present holder assembly also facilitates relatively fast exchanges of solutions and media utilized in the perfusion procedures.

Having shown and described the preferred embodiments of the present invention, further adaptions of the holder assembly and flow cell arrangement of the present invention can be accomplished by appropriate modifications by one of ordinary skill in the art without departing from the scope of the present invention. Several of such potential modifications have been mentioned, and others will be apparent to those skilled in the art. For example, while clamp 60 has been shown and described as being hingedly attached adjacent the bottom end of the holder body, other convenient attachment means and arrangements could be equally substituted as appropriate.

Accordingly, the scope of the present invention should be considered in terms of the following claims, and is understood not to be limited to the details of structure and operation shown and described in the specification and drawings.

We claim:

1. A holder assembly for a coverslip, said holder adapted for use in conjunction with a sample vessel and a device for assaying the light absorbing, reflecting or other optical characteristics of substances on such coverslip, and a holder body having spaced front and rear faces, and top and bottom ends, with said front face having a substantially planar portion, means located adjacent the bottom end of said front face for supporting a coverslip substantially flush with said planar portion, and a non-reflecting light sink; and a clamp releasably attachable to said holder body, said clamp comprising means for maintaining a coverslip in substantially flush supported position relative to said front face of said holder body, and a light permeable portion generally aligned with said planar portion when in attached position with said holder body.

2. The holder assembly of claim 1, further comprising means for hingedly attaching said clamp to said holder body, whereby said clamp may be articulated between open and attached positions.

3. The holder assembly of claim 2, wherein said clamp further comprises a hinged connection with said holder body adjacent one of said top and bottom ends, and means for locking said clamp in attached position with said holder body.

4. The holder assembly of claim 1, wherein said holder body is provided as a unitary structure having means for biasing said holder assembly outwardly against a sample vessel.

5. The holder assembly of claim 4, wherein said sample vessel is a cuvette, and wherein said biasing means comprises at least one compressible portion formed within said holder body.

6. The holder assembly of claim 1, further comprising means for enabling perfusion of cells on said coverslip while said coverslip is held within said assembly.

7. The holder assembly of claim 1, wherein said clamp comprises an inwardly facing portion having at least one support protuberance which extends inwardly to resiliently secure a coverslip between said holder body and said clamp in attached position.

8. The holder assembly of claim 2, wherein said clamp further comprises a hinged connection with said holder body adjacent one of said top and bottom ends, and snap fit means for releasably locking said clamp in attached position with said holder body.

9. The holder assembly of claim 1, wherein said holder body and said clamp provide an exterior conformation which substantially corresponds to the inner conformation of a sample vessel when in attached position.

10. An assembly for holding a coverslip upon which cells may be cultured for study within a sample vessel and device for assaying the light absorbing, reflecting or optical characteristics of such cells, said holder comprising:

a holder body having spaced front and rear faces, top and bottom ends, and a nonreflecting light path between said front and rear surfaces, said front face having a substantially planar portion and means located adjacent the bottom end of said front face for supporting a coverslip substantially flush with said planar portion; and a clamp which is hingedly attached to said holder body, said clamp comprising means for maintaining a coverslip in substantially flush supported position relative to said front face of said holder body and a light permeable portion aligned with said light path when in attached position with said holder body, said clamp being rotatable away from said front face to facilitate coverslip loading, unloading and cleaning procedures.

11. The assembly of claim 10, wherein said clamp is hingedly attached to said holder body adjacent one of said top and bottom ends, and further comprising means for locking said clamp in attached position with said holder body.

12. The assembly of claim 11, wherein said locking means comprises an interacting snap lock and corresponding groove arrangement adjacent the top ends of said holder body and clamp, respectively.

13. The holder assembly of claim 10, wherein said holder body is provided as a unitary structure having means for biasing said holder assembly outwardly against the inside of a sample vessel.

14. The holder assembly of claim 13, wherein said sample vessel is a cuvette, and wherein said biasing means comprises at least one spring slot formed in said holder body.

15. The holder assembly of claim 10, further comprising means for enabling perfusion of cells on said coverslip while said coverslip is held within said assembly.

16. The holder assembly of claim 10, wherein said clamp comprises an inwardly facing portion having at least one support protuberance extending to resiliently secure a coverslip between said holder body and said clamp in attached position.

17. An assembly for holding a coverslip upon which cells may be cultured for study within a cuvette and device for front face measurement of fluorescence of such cells, said holder comprising:
- a holder body having spaced front and rear faces, top and bottom ends, and a relatively hollow light path extending between said front and rear surfaces, said front face having a substantially planar portion and means located adjacent the bottom end of said front face for supporting a coverslip substantially flush with said planar portion;
- a clamp which is hingedly attached to said holder body, said clamp comprising a light permeable sight path substantially aligned with said light path when in attached position with said holder body; and
- means for selectively locking said clamp in attached position adjacent said front face of said holder body, wherein said coverslip is held in substantially flush supported position relative to said front face and aligned with said sight path.

18. The assembly of claim 17, wherein said holder body is provided as a unitary structure having means for biasing said assembly outwardly against the inside of a cuvette with said front face and a supported coverslide located closely adjacent and normal to the incident light of said device for measuring the fluorescence of said cells on the coverslide.

19. The holder assembly of claim 17, further comprising means for enabling perfusion of cells on said coverslip while said coverslip is held within said assembly.

20. The holder assembly of claim 18, wherein said sample vessel is a cuvette, and wherein said biasing means comprises at least one spring slot formed in said holder body.

* * * * *

UNITED STATES PATENT AND TRADEMARK OFFICE
CERTIFICATE OF CORRECTION

PATENT NO. : 5,208,649
DATED : May 4, 1993
INVENTOR(S) : John Cuppoletti & Nick H. Langdon It is certified that error appears in the above—identified patent and that said Letters Patent is hereby corrected as shown below:

In column 7, claim 1, line 44, insert " said holder comprising:" after --and--

Signed and Sealed this

Twenty-fifth Day of January, 1994

Attest:

BRUCE LEHMAN

*Attesting Officer*    *Commissioner of Patents and Trademarks*